| United States Patent [19] | [11] Patent Number: 4,785,014 |
| Goldman-Rakic et al. | [45] Date of Patent: Nov. 15, 1988 |

[54] USE OF CLONIDINE IN MEMORY ENHANCEMENT

[75] Inventors: Patricia S. Goldman-Rakic, Hamden; Amy F. T. Arnsten, Bethany, both of Conn.

[73] Assignee: Yale University, New Haven, Conn.

[21] Appl. No.: 927,900

[22] Filed: Nov. 6, 1986

Related U.S. Application Data

[63] Continuation of Ser. No. 742,344, Jun. 7, 1985, abandoned.

[51] Int. Cl.[4] .............................................. A61K 31/415
[52] U.S. Cl. ..................................... 514/401; 514/930
[58] Field of Search ................................ 514/401, 930

[56] References Cited

PUBLICATIONS

Quartermain et al., Pharmacology Biochemistry & Behavior 7:259–267 (1977).
Freeman et al., Pharmacology Biochemistry & Behavior, 4:259–263 (1979).

*Primary Examiner*—Stanley J. Friedman
*Attorney, Agent, or Firm*—David E. Frankhouser; Alan R. Stempel; Mary-Ellen M. Timbers

[57] ABSTRACT

Disclosed is a method of treating cognitive decline in a normal aged primate by administering thereto a therapeutically effective amount of 2-[(2,6-dichlorophenyl)-amino]-2-imidazoline or a nontoxic, pharmaceutically acceptable salt thereof. Administration is preferably in amounts of at least about 0.001 mg/day.

12 Claims, 4 Drawing Sheets

USE OF CLONIDINE IN MEMORY ENHANCEMENT

This is a continuation of application Ser. No. 742,344, filed June 7, 1985, now abandoned.

BACKGROUND OF THE INVENTION

1. Field of the Invention

The present invention relates to the improvement of memory in normal aged primates, particularly to the improvement of short term memory in aged primates.

2. Brief Information Disclosure Statement

Clonidine, also known as 2-[(2,6-dichlorophenyl)amino]-2-imidazoline is well known as a potent antihypertensive sold under the registered trademark CATAPRES®, brand of clonidine hydrochloride. It has been extensively described in the literature, including U.S. Pat. No. 3,202,660; Goodman and Gilman (Eds.), *Pharmacological Basis of Therapeutics*, 6th Ed, MacMillan Publishing Co., Inc., N.Y. (1980) p 797; THE MERCK INDEX, 9th Ed, Merck & Co., Inc., Rahway, N.J., U.S.A., Abstract 2352. page 797; and PHYSICIANS' DESK REFERENCE, 38th Ed., 1984, Medical Economics Company, Inc., Oradell, N.J., p 692.

Clonidine has been studied for its effect on patients suffering from the alcohol-related vitamin deficiency known as Korsakoff's syndrome and was associated with memory improvement in such patients as measured by neuropsychological testing. McEntee, et al, *Ann. Neurol*, 7:466–470 (1980) and McEntee, et al, *Psychopharmacol. Bull.*, 17: 123–124 (1981) See, also, Psychopharmacology of Clonidine, Alan R. Liss, Inc. (N.Y.), pgs. 211–223 (1981).

In another study of Korsakoff patients, an enhancement of episodic memory was observed compared to predrug values in patients during withdrawal from clonidine treatment. Martin, et al, *Psychopharmacology*. 84:58–63 (1984).

SUMMARY OF THE INVENTION

In accordance with the present invention, it has been discovered that 2-[2,6-dichlorophenyl)amino]-2-imidazoline and its nontoxic, pharmaceutically acceptable salts are useful in treating cognitive disorders in normal aged primates, including humans and simian species, and further in the improvement of cognitive performance in such aged normal primates. In one aspect, this provides a method of treating age-related cognitive disorders associated wtih catecholamine deficiency in aged normal primates by administering thereto a therapeutically effective amount of 2-[(2,6-dichlorophenyl)-amino]-2-imidazoline or a nontoxic, pharmaceutically acceptable salt thereof. In another aspect, the invention also provides a method of improving age related cognitive performance in an aged normal primate which method comprises administering thereto a therapeutically effective amount of 2-[(2,6-dichlorophenyl)-amino]-2-imidazoline or a nontoxic pharmaceutically acceptable salt thereof.

Dosages of from at least about 0.001 mg/kg, up to at least about 0.1 mg/kg are effective from initial administration, preferably by injection or orally, when administered for periods of at least about two weeks up to a continuing maintenance regimen in excess of 2 years. Dosages within this range can be administered at intervals sufficient to maintain a therapeutic effect, from multiple daily doses to single doses on non-sequential days.

DETAILED DESCRIPTION OF PREFERRED EMBODIMENTS

Figure 1:
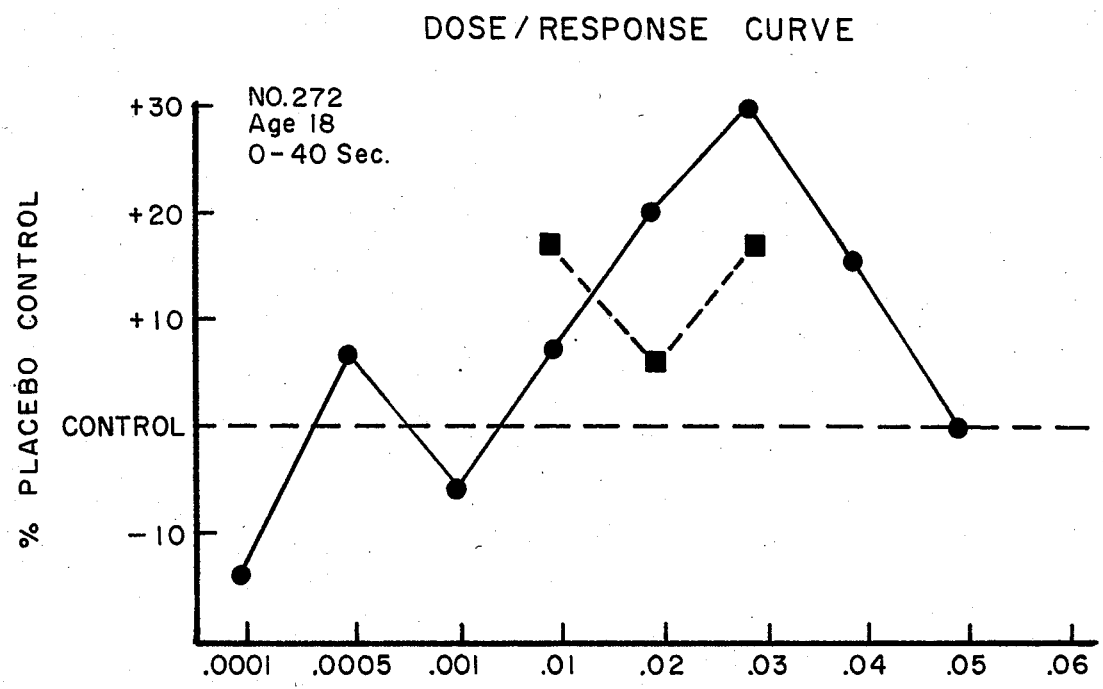
FIGS. 1A–1E show individual clonidine dose/response curves (solid curves) for the 5 aged rhesus monkeys tested upon the delayed response task. Hatched curves illustrate replications of selected doses; asterisks indicate that the animal was too sedated to test.
FIG. 1F shows a representative delay/response function for animal (C).
Figure 1:
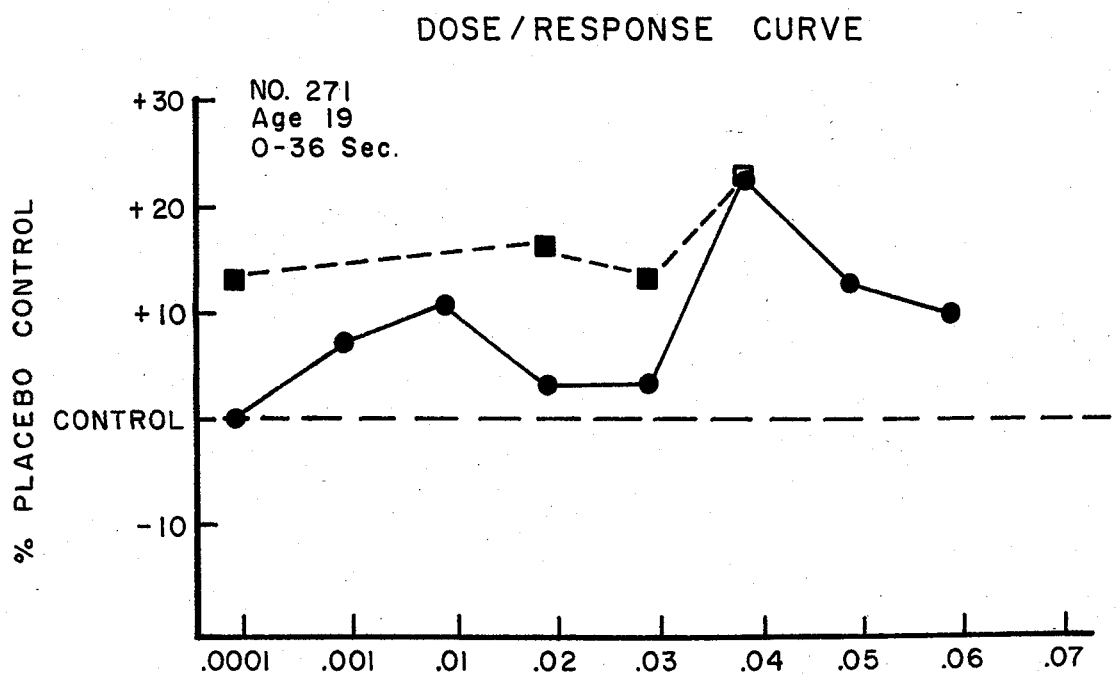
Figure 1C:
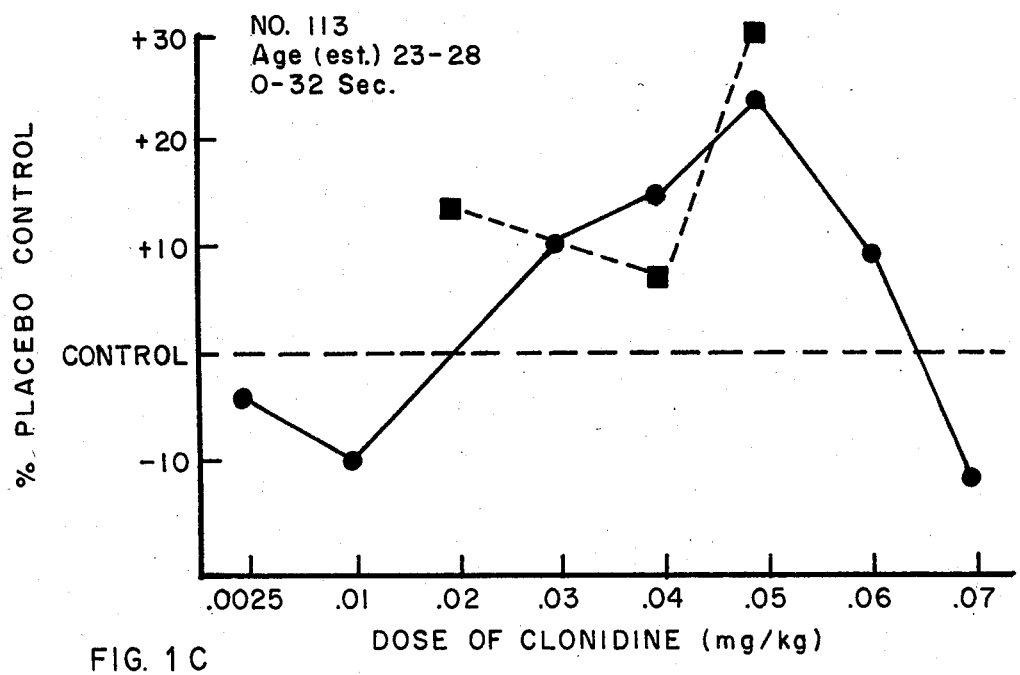

The present invention is based on the observation that the administration of 2-[(2,6-dichlorophenyl)amino]-2-imidazoline or a nontoxic, pharmaceutically acceptable salt thereof has been effective in treating age-related cognitive decline and improving cognitive performance in normal aged primates. This has been particularly noted in improvements relating to short term memory, in treating short term memory deficits and in improving short term memory in aged subjects. Clonidine has been highly effective in this regard as compared to other compounds which were examined.

The present invention also provides the observation that clonidine is useful in treating age-related disorders in which short-term memory loss is associated with catecholamine dysfunction in the brain. It has recently been established that the catecholamine, norepinephrine, is markedly decreased in Alzheimer's Disease. See Adolfsson et al., *Brit. J. Psychiat.*, 135: 216–223 (1979); Benton et al., Lancet, 20: 456 (1982); Perry et al., *J. Neurol. Sci.*, 51: 279–287, (1981); Forno, *Neuropath. Exp. Neurol.*, 37: 614 (1978); Tomlinson et al., *J. Neurol. Sci.*, 49: 419–428 (1981) and Iversen et al., *Neurosci. Letters*, 39: 95–100 (1983). The research described below indicates that clonidine can improve short-term memory by replacing lost norepinephrine activity at alpha receptors.

The experiments described here report an evaluation of the effects of catecholaminergic agonists on cognitive performance in five female rhesus monkeys ranging in age from 17 to over 30 years. Monkeys in this age range are known to have naturally-occurring catecholamine loss. See Goldman-Rakic and Brown, *Neurosci.*, 6: 177–187 (1981) and Sladek and Blanchard, *Aging*, 17: 13–21, (1981). The aged animals are trained on a delayed reponse task which is sensitive to aging as described in R.T. Bartus, D. Fleming, H.R. Johnson, *J. Gerontology* 33, 858 (1978).

To observe the effects of each drug on mnemonic capacity, the delays used are varied between "0" seconds and the temporal interval at which each animal performs at chance. Five different delay lengths are used in the 30 trials which made up a daily test session. Each monkey is tested twice a week, once shortly after a single dose of drug and once with a placebo treatment. The sequence of drug and placebo treatment is varied from week to week.

The drugs which were tested are as follows: clonidine (0.0001–0.08 mg/kg; Boehringer-Ingelheim); levo-dopa and carbi-dopa (10–50 mg/kg and 5–20 mg/kg; Merck, Sharp and Dohme); apomorphine (0.001–0.06 mg/kg; Merck, Sharp and Dohme); propranolol (0.01–1.0 mg/kg; Ayerst); diazepam (0.1–0.5 mg/kg; Hoffman La Roche); and yohimbine (0.1–1.5 mg/kg; Sigma). Clonidine, propranolol and yohimbine were injected intramuscularly 15 minutes before testing; L-dopa/carbidopa and diazepam were mixed into banana and fed 90 and 30 minutes prior to testing, respectively.

The aged animals perform very consistently over the 18 months of the study. The individual clonidine dose/response curves are shown in FIGS. 1A–1E. The range of delays used for each animal is indicated; the data present the total percent correct irrespective of delay. Performance on clonidine is calculated as the percentage change from matched placebo control performance. Four of the five aged monkeys exhibited near perfect performance (+30%) following the most effective dose of clonidine. The overall performance on placebo averages 64% ±6% correct, with errors occurring mostly at the longer delays. See, for example, FIG. 1F. Results from a single intramuscular dose of clonidine (0.05 mg/kg) are represented by the solid curve; the improvement in performance was most marked at the longer delays. Saline placebo performance is indicated by the hatched curve; the animal performed well at short delays and more poorly as the delay lengthened. In addition, there is an inverse relationship between the age of the animal and the length of the delays at which they perform correctly, with the youngest monkeys performing better at the longest delays (eg monkey A, 0–40 sec. FIG. 1A).

The alpha-2 receptor agonist, clonidine, improves delayed response performance in every one of the 5 aged monkeys. At the most effective clonidine dose, 4 of the 5 animals achieve near perfect performance (FIGS. 1A–1E).

Figure 1D:
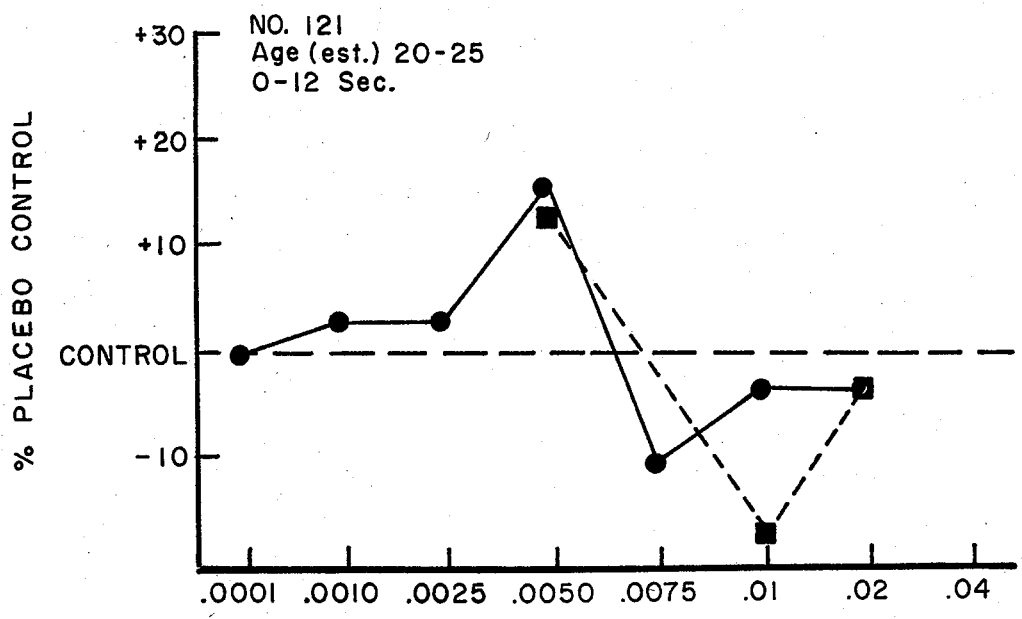
Figure 1:
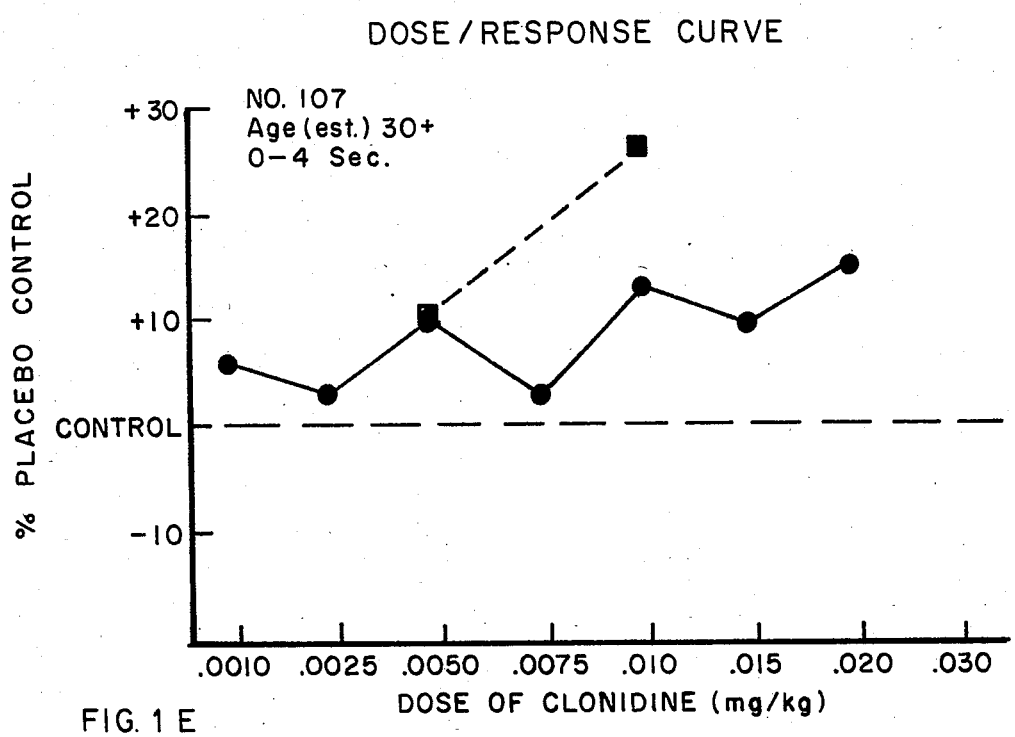
Figure 1:
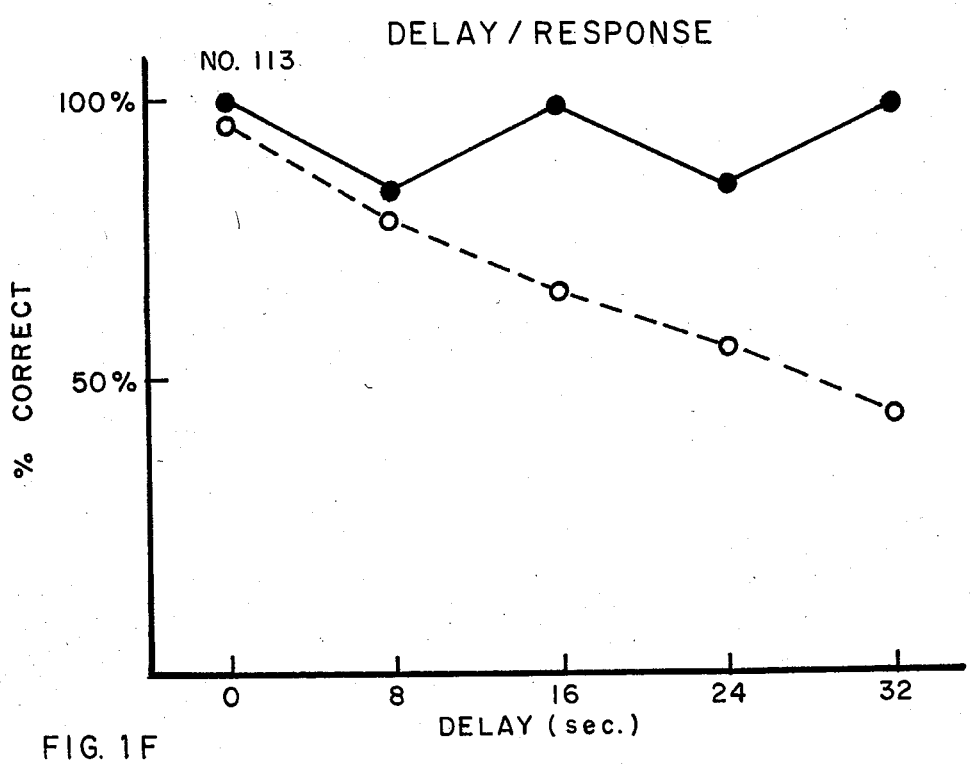

At the highest dose the aged animals are impeded by clonidine's sedative effects. However, every animal appears to develop tolerance to this side effect. In some animals, tolerance to clonidine's sedative effects must develop before the beneficial effects of the drug can be observed. This is true of the monkey (D) which is not consistently improved by acute injections of the drug (FIG. 1D). However, the repeated administration of 0.02 mg/kg clonidine results in a reliable improvement in delayed response performance.

Marked improvements with clonidine are found with the oldest (+30 years) monkey who performs 93% correctly following the 0.01 mg/kg dose (FIG. 1E). It is notable that in every animal, clonidine's beneficial effects are most apparent at the longer delays (eg FIG. 1F).

Figure 2A:
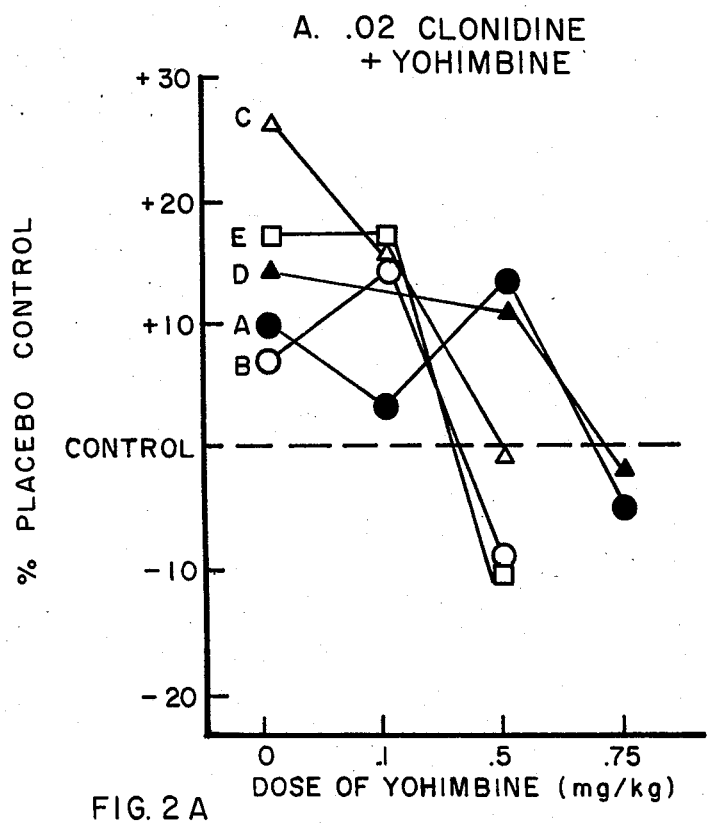
FIG. 2A shows the ability of increasing doses of the alpha-2 antagonist yohimbine to block the response to 0.02 mg/kg clonidine. The data present the total percent change from placebo control performance irrespective of delay.
Figure 2B:
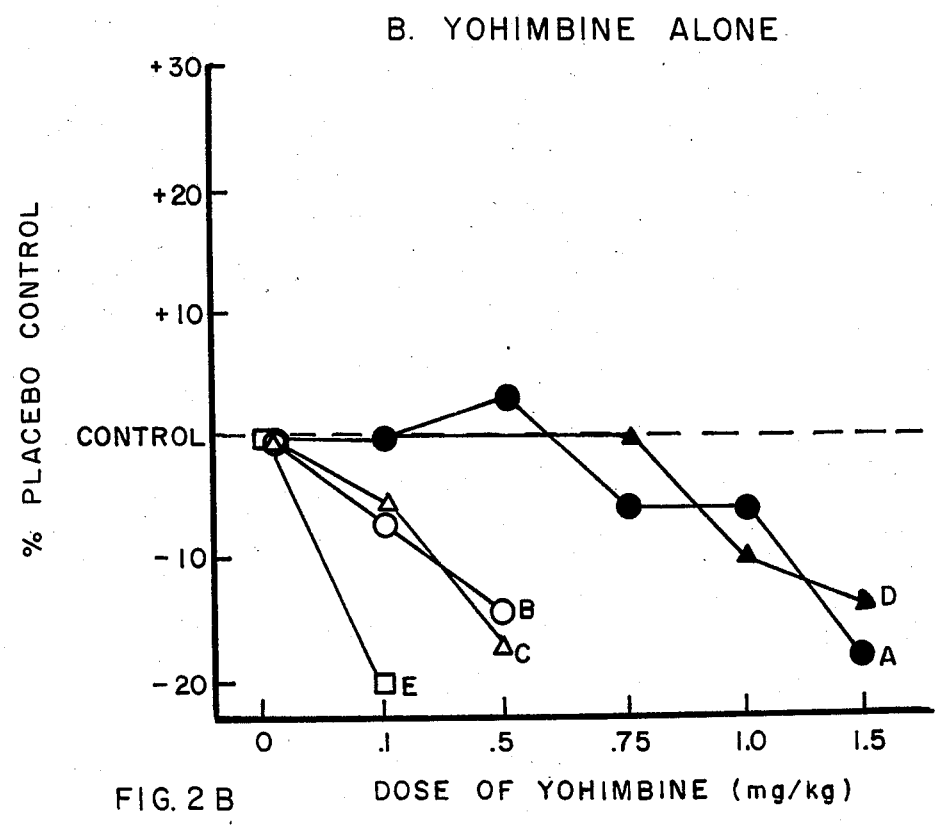
FIG. 2B shows that yohimbine administered by itself impairs performance below placebo control to chance levels of responding (approx. −15%).

Improvements in cognitive performance by clonidine appear to result from actions at alpha-2 adrenergic receptors, as they were blocked by the alpha-2 antagonist, yohimbine, in a dose-dependent manner (FIG. 2A). Furthermore, the administration of yohimbine alone actually exaggerates cognitive deficit in certain cases. (FIG. 2B). As shown in FIG. 2B, the performance of the oldest animal (E) is worsened by the lowest dose to yohimbine tested (0.1 mg/kg). The younger monkeys need increasingly higher doses (0.5–1.5 mg/kg) to produce marked impairments. The youngest monkey (A) is worsened by the highest dose of the drug (1.5 mg/kg). Impairments are not seen with the beta receptor antagonist, propranolol. At the most effective dose, propranolol (1.0 mg/kg) delayed response performance is altered by +1%±4%.

To examine the specificity of clonidine's effects on cognitive function, the aged monkeys are trained on a visual pattern discrimination task which does not rely on working memory. The oldest animals perform poorly on this task. However, they are not improved by doses of clonidine which facilitated their delayed response performance (saline—59%± 3%, clonidine—55%±3%). Conversely, the two youngest monkeys perform well on the visual discrimination task, and are not impeded by doses of yohimbine which reduce delayed response performance to chance levels of responding (saline—100%±0%, yohimbine—100%±0%). The absence of clonidine and yohimbine effects on the visual discrimination task indicates that these alpha-2 agents are not affecting delayed response performance through a general alteration of levels of motivation, anxiety, alertness or blood pressure; nonspecific consequences that would be expected to affect performance on both types of tasks. Consonant with this interpretation are the findings that neither the hypotensive agent, propranolol, nor the sedative, diazepam, alter the delayed response performance of the aged monkeys. At the most effective dose, propranolol (1.0 mg/kg) alters delayed response performance by +1%±4% and diazepam (0.1–0.5 mg/kg) alters performance by 0%±7%. Rather, clonidine and yohimbine have direct effects on cognitive function, and particularly most mnemonic functions utilized in the performance of the delayed response task.

Although the invention has been described with particularity, one skilled in the field can resort to numerous changes in the details, combinations and arrangements of elements without departing from the scope of the invention.

What is claimed is:

1. A method of treating age-related cognitive decline in a normal aged primate which method comprises administering thereto a therapeutically effective amount of 2-[(2,6-dichlorophenyl)amino]-2-imidazoline or a nontoxic pharmaceutically acceptable salt thereof.

2. The method of claim 1 which comprises treating an age-related short term memory deficit.

3. The method of claim 1 which comprises treating age-related cognitive decline associated with subnormal catecholamine levels.

4. The method of claim 1 which comprises administering a therapeutically effective amount of 2-[(2,6-dichlorophenyl)-amino]-2-imidazoline hydrochloride.

5. The method of claim 1 which comprises administering at least about 0.001 mg/kg daily of [(2,6-dichlorophenyl)amino]-2-imidazoline or a nontoxic, pharmaceutically acceptable addition salt thereof.

6. The method of claim 5 which comprises administering from about 0.001 mg/kg to at least about 0.1 mg/kg of 2-[(2,6-dichlorophenyl)amino]-2-imidazoline or a nontoxic, pharmaceutically acceptable addition salt thereof.

7. A method of improving cognitive performance in an normal aged primate which method comprises administering thereto a therapeutically effective amount of 2-[(2,6-dichlorophenyl)amino]-2-imidazoline or a nontoxic pharmaceutically acceptable salt thereof.

8. The method of claim 7 which comprises improving short-term memory.

9. The method of claim 8 which comprises improving short-term memory-related task performance.

10. The method of claim 7 which comprises administering a therapeutically effective amount of 2-[(2,6-dichlorophenyl)-amino]-2-imidazoline hydrochloride.

11. The method of claim 7 which comprises administering at least about 0.001 mg/kg of 2-[(2,6 - dichlorophenyl)amino]-2-imidazoline or a nontoxic, pharmaceutically acceptable salt thereof.

12. The method of claim 11 which comprises administering from about 0.001 mg/kg to at least about 0.1 mg/kg of 2-[(2,6 -dichlorophenyl)-amino]-2-imidazoline or a nontoxic, pharmaceutrically acceptable salt thereof.

* * * * *